(12) United States Patent
Wen

(10) Patent No.: US 10,301,442 B2
(45) Date of Patent: May 28, 2019

(54) METHOD FOR PREPARING A CELLULOSE SPONGE AND MIXED SOLUTION THEREOF

(71) Applicant: PISHON BIOMEDICAL CO., LTD., Taipei (TW)

(72) Inventor: Sheng-Tung Wen, Taipei (TW)

(73) Assignee: PISHON BIOMEDICAL CO., LTD, Taipei (TW)

(*) Notice: Subject to any disclaimer, the term of this patent is extended or adjusted under 35 U.S.C. 154(b) by 38 days.

(21) Appl. No.: 15/372,382

(22) Filed: Dec. 7, 2016

(65) Prior Publication Data

US 2018/0072855 A1  Mar. 15, 2018

(30) Foreign Application Priority Data

Sep. 12, 2016 (CN) .......................... 2016 1 0817024

(51) Int. Cl.
*C08J 3/28* (2006.01)
*C12N 5/00* (2006.01)
*C08J 9/28* (2006.01)
*C08J 3/075* (2006.01)

(52) U.S. Cl.
CPC ................. *C08J 3/28* (2013.01); *C08J 3/075* (2013.01); *C08J 9/28* (2013.01); *C12N 5/0062* (2013.01); *C08J 2201/026* (2013.01); *C08J 2201/0502* (2013.01); *C08J 2205/024* (2013.01); *C08J 2205/028* (2013.01); *C08J 2205/044* (2013.01); *C08J 2207/00* (2013.01); *C08J 2301/26* (2013.01); *C12N 2533/78* (2013.01)

(58) Field of Classification Search
CPC ................................ C08J 3/28; C08J 2301/28
See application file for complete search history.

(56) References Cited

PUBLICATIONS

Yue et al., "Preparation of three-dimensional interconnected macroporous cellulosic hydrogels for soft tissue engineering," Biomaterials 31 (2010) pp. 8141-8152. (Year: 2010).*

* cited by examiner

Primary Examiner — Kara B Boyle
(74) Attorney, Agent, or Firm — Hannah M. Tien

(57) ABSTRACT

The present invention relates to a method for preparing a cellulose sponge, comprising: (A) providing a solution of hydroxypropyl cellulose having a self-crosslinkable substituent; and (B) irradiating the solution of hydroxypropyl cellulose having the self-crosslinkable substituent with γ-ray for crosslinking, wherein a method for preparing the hydroxypropyl cellulose having the self-crosslinkable substituent comprises: (a) dissolving hydroxypropyl cellulose in dimethylformamide to form a hydroxypropyl cellulose solution; (b) dissolving a compound comprising the self-crosslinkable substituent in dimethylformamide and slowly adding it drop by drop into the hydroxypropyl cellulose solution; (c) adding alcohol for reaction; and (d) reacting and drying at room temperature to form the hydroxypropyl cellulose having the self-crosslinkable substituent. The present invention also relates to a mixed solution, comprising dimethylformamide, hydroxypropyl cellulose, a compound comprising a self-crosslinkable substituent and alcohol.

9 Claims, 5 Drawing Sheets

METHOD FOR PREPARING A CELLULOSE SPONGE AND MIXED SOLUTION THEREOF

CROSS-REFERENCES TO RELATED APPLICATIONS

The present application claims priority to China Patent Application No. 201610817024.5 filed on Sep. 12, 2016, incorporated herein by reference in its entirety.

FIELD OF THE INVENTION

The present invention relates to a method for preparing a cellulose sponge and a mixed solution thereof.

BACKGROUND OF THE INVENTION

Cell culture and tissue engineering are critical technologies in regenerative medicine, which provides sufficient cells for experimental analysis through large-scale proliferation by artificial means, and then conditions required for the growth and development of tissue cells are simulated and provided, thereby enabling cells obtained by culture to grow and differentiate into cells or tissues with specific characteristics.

Regenerative medicine provides solutions to problems such as uncertainties of organ donation and potential graft rejections due to immune responses following organ transplantation. However, its development is limited by a few techniques, for example, cell culture and three dimensional scaffolds.

In the field of biological cells, it is generally believed that the biomimetic activity of a three-dimensional culture is better than that of a two-dimensional monolayer culture. A number of three-dimensional cell culture methods have thus developed, such as a hydrogel, a suspension, a hanging drop culture, a micromass culture, and a non-adherent substrate. In the field of cell culture, in order for the cultured cells to grow into tissues or organs with desired functions and forms, the use of scaffolds plays an important role. The function of the scaffold is to provide a three-dimensional framework suitable for cell growth, which is commonly known as a three-dimensional scaffold. It has a large number of pores for cell attachments or inoculations, guiding the cells to grow and differentiate in three-dimensional directions as planned to produce simulated and regenerated tissues or organs.

In traditional flat cell culture, there is only a very small area of contact between cells, half of the surface area of a cell is in contact with the culture plate, and the other half is in contact with the culture medium. A three-dimensional culture environment provides other advantages, it is capable of: providing better biochemical signals to direct cell functions, allowing cell migration within the scaffold, increasing cell density and increasing signal transmission among cells, providing molecules for cell attachments and for inducing cell differentiation. When the pore size of a sponge-like three-dimensional scaffold is greater than 50 μm, cell migration is enhanced and more uniform distribution of seeded cells and nutrients are facilitated by the inter-connecting porous structure.

Therefore, one of the important issues in the field is to provide a method and a device for preparing a three-dimensional scaffold, which can achieve the purpose of preparing the three-dimensional scaffold in a simple manner with simple devices, allowing cells to be cultivated stably and grow eventually into tissues or organs with desired functions and forms.

In view of the foregoing, an object of the present invention is to provide a method for preparing a cellulose sponge and a mixed solution thereof, which can achieve the purpose of preparing the three-dimensional scaffold in a simple manner and in a solution, thereby simplifying the complicated process for preparing the scaffold and shortening the required preparation time.

SUMMARY OF THE INVENTION

Figure 1:
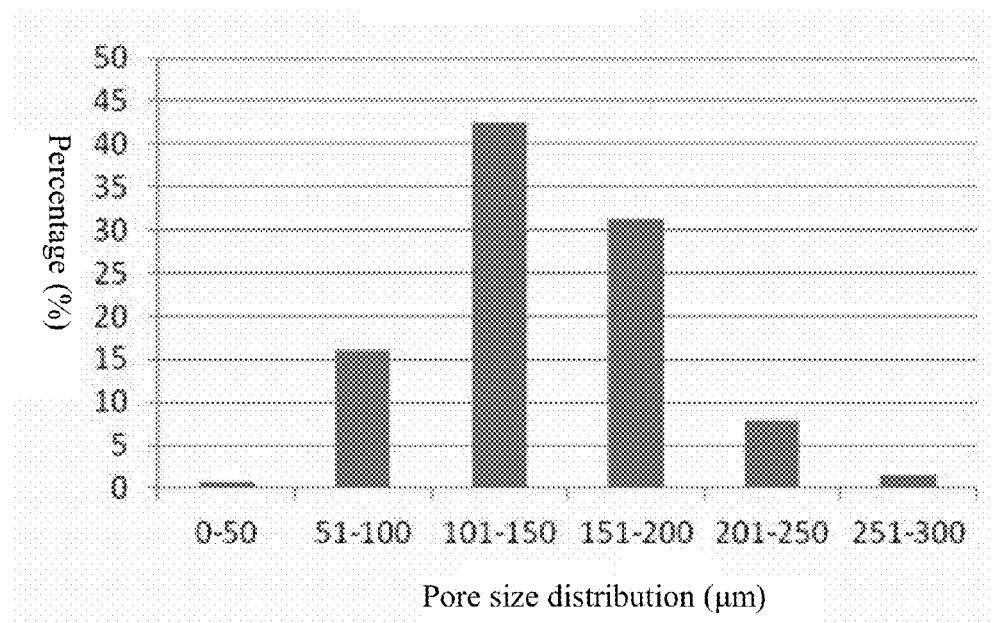
FIG. 1 is a diagram showing the pore size distribution of the cellulose sponge with additionally added alcohol of the present invention.

The present invention provides a method for preparing a cellulose sponge, comprising: (A) providing a solution of hydroxypropyl cellulose having a self-crosslinkable substituent; and (B) irradiating the solution of hydroxypropyl cellulose having the self-crosslinkable substituent with γ-ray for crosslinking, wherein a method for preparing the hydroxypropyl cellulose having the self-crosslinkable substituent comprises: (a) dissolving hydroxypropyl cellulose in dimethylformamide to form a hydroxypropyl cellulose solution; (b) dissolving a compound comprising the self-crosslinkable substituent in dimethylformamide and slowly adding it drop by drop into the hydroxypropyl cellulose solution; (c) adding alcohol for reaction; and (d) reacting and drying at room temperature to form the hydroxypropyl cellulose having the self-crosslinkable substituent. The present invention also provides a mixed solution, comprising dimethylformamide, hydroxypropyl cellulose, a compound comprising a self-crosslinkable substituent and alcohol.

DETAIL DESCRIPTION OF THE INVENTION

Unless otherwise specified, "a" or "an" means "one or more".

The term "cellulose sponge" as used herein includes a three dimensional structure of any shape, size, or composition, which can be used as a structure for attachment, adherence or implantation of at least one kind of cell and can serve the purpose of promoting normal cell growth and/or proliferation and/or differentiation. In one embodiment of the present invention, since the cellulose sponge prepared by the method and the mixed solution disclosed in the present invention are oriented for medical use, the cellulose sponge is preferably used in a biocompatible manner. In another embodiment of the present invention, the cellulose sponge prepared by the method and the mixed solution disclosed in the present invention is used for cell culture and the cellulose sponge has high air permeability and nutrient permeability (i.e., a better specific surface area).

The present invention provides a method for preparing a cellulose sponge, comprising: (A) providing a solution of hydroxypropyl cellulose having a self-crosslinkable substituent; and (B) irradiating the solution of hydroxypropyl cellulose having the self-crosslinkable substituent with γ-ray for crosslinking, wherein a method for preparing the hydroxypropyl cellulose having the self-crosslinkable substituent comprises: (a) dissolving hydroxypropyl cellulose in dimethylformamide to form a hydroxypropyl cellulose solution; (b) dissolving a compound comprising the self-crosslinkable substituent in dimethylformamide and slowly adding it drop by drop into the hydroxypropyl cellulose solution; (c) adding alcohol for reaction; and (d) reacting and drying at room temperature to form the hydroxypropyl cellulose having the self-crosslinkable substituent.

According to the method of the present invention, in one preferred embodiment, the compound comprising the self-crosslinkable substituent comprises but is not limited to allyl isocyanate, methacrylic acid, acrylic acid, or glycidyl methacrylate.

According to the method of the present invention, in one preferred embodiment, the volume of the alcohol is 1.5-50% of the total volume of the dimethylformamide; in another preferred embodiment, the volume of the alcohol is 7.5-40% of the total volume of the dimethylformamide; in yet another preferred embodiment, the volume of the alcohol is 10-35% of the total volume of the dimethylformamide.

According to the method of the present invention, in one preferred embodiment, the alcohol comprises but is not limited to methanol, ethanol, propanol or butanol.

The present invention further provides a mixed solution, which comprises dimethylformamide, hydroxypropyl cellulose, a compound comprising a self-crosslinkable substituent and alcohol.

Since alcohol is added in the mixed solution of the present invention, the added alcohol is capable of increasing dispersibility and stability of solutes to yield a structurally stable cellulose sponge. In one preferred embodiment, the compound having the self-crosslinkable substituent comprises but is not limited to allyl isocyanate, methacrylic acid, acrylic acid, or glycidyl methacrylate.

According to the mixed solution of the present invention, in one preferred embodiment, the volume of the alcohol is 1.5-50% of the total volume of the dimethylformamide; in another preferred embodiment, the volume of the alcohol is 7.5-40% of the total volume of the dimethylformamide; in yet another preferred embodiment, the volume of the alcohols is 10-35% of the total volume of the dimethylformamide.

According to the mixed solution of the present invention, in one preferred embodiment, the alcohol comprises but is not limited to methanol, ethanol, propanol or butanol.

EXAMPLES

The examples below are non-limiting and are merely representative of various aspects and features of the present invention.

Preparation of Cellulose Sponge

Preparation of the cellulose sponge with additionally added alcohol of the present invention was divided into two steps:

1. Synthesis of hydroxypropyl cellulose having a substituent:
   (1) Hydroxypropyl cellulose (HPC) ($M_n \approx 10,000$) was dehydrated by azeotropic distillation in toluene.
   (2) 3.0 g dehydrated HPC was dissolved in 120 ml of dimethylformamide (DMF);
   (3) 3.84 ml of allyl isocyanate was dissolved in 5 ml of dimethylformamide and then was slowly added drop by drop to the above prepared hydroxypropyl cellulose solution;
   (4) 37.5 ml of alcohol (such as propanol) was added for reaction, the volume of the alcohol is 30% of the total volume of dimethylformamide (dimethylformamide 125 ml×30%=37.5 ml, the volume ratio of dimethylformamide:alcohol=3.3:1);
   (5) One drop of dibutyltin dilaurate was added as a catalyst;
   (6) Stirred at room temperature for 48 hours;
   (7) The volume was reduced by using a rotatory evaporator and then the polymer was separated by ether; and
   (8) The reaction products were collected by vacuum filtration and precipitated into diethyl ether; the residual impurities were removed by Soxhlet extraction from diethyl ether to form hydroxypropyl cellulose having the substituent.

2. Gamma ray irradiation
   (1) Hydroxypropyl cellulose having a substituent in dry form was formulated into a 10 wt % aqueous solution and placed in a glass tube (diameter 10 mm×height 50 mm);
   (2) Temperature testing procedure: the aqueous solution changed from transparent into opalescent, a temperature controller was used to control the temperature, the sample stayed for a period of time at each temperature when the temperature was increased in order to observe color changes visually. When creamy-white color was observed but without the formation of layers and precipitations (indicating the formation of a stable colloidal system which was beneficial to subsequent formation of a three dimensional porous structure), the corresponding temperature was recorded and the temperature ranged from 38~45° C. The recorded temperature would be used in subsequent gamma-ray irradiation for crosslinking
   (3) Irradiated with gamma ray at the above recorded temperatures; and
   (4) The hydroxypropyl cellulose having the substituent solidified after irradiation, the finish product was obtained after washing and freeze-drying.

The method for preparing the cellulose sponge without additionally added alcohol of the present invention was the same as described above, except that no alcohol was additionally added in step 1, i.e., step (4) of step 1 was skipped.

Appearance and Pore Size Measurement of Cellulose Sponge

The diameter and thickness of the cellulose sponge with additionally added alcohol in dry form and in wet form were measured, and the results were shown as in Table 1.

TABLE 1

Appearance and size of the cellulose sponge with additionally added alcohol

|  | Diameter | Thickness |
| --- | --- | --- |
| In dry form | 9.0 mm | 1.0 mm |
| In wet form | 9.0 mm | 1.0 mm |

As shown in Table 1, the diameter of the cellulose sponge with additionally added alcohol was 9 mm, which would be suitable to be placed in 48-well plates and easy to be used with ordinary cell culture devices. The thickness of the cellulose sponge with additionally added alcohol was 1 mm, which would avoid the problem of being too thick for an optical microscope to perform a preliminary observation. Therefore, the cellulose sponge with additionally added alcohol would be easier to be used with commonly available cell culture devices.

Software image J was subsequently used for statistical analysis of the pore size of the cellulose sponge with additionally added alcohol; the results were shown in FIG. 1 and Table 2.

TABLE 2

Pore size distribution of cellulose sponge with additionally added alcohol of the present invention
Pore size distribution

| Pore size range (μm) | Percentage % |
| --- | --- |
| 0-50 | 0.8 |
| 51-100 | 16 |
| 101-150 | 42.4 |
| 151-200 | 31.2 |
| 201-250 | 8 |
| 251-300 | 1.6 |

By analyzing pore sizes, it was found that the pore size of the cellulose sponge with additionally added alcohol was 50~250 μm, pores of this size would provide cells with an appropriate growth environment. Limiting the size of the pore to certain degree would limit the size of a cell cluster, thereby avoiding distortion of the three-dimensional structure of the cells due to oversized pores, or cell death in the center of a cluster due to the oversized cell cluster.

Structure of Cellulose Sponge

A cellulose sponge in dry form was placed on a dish, and the pore morphology was observed by using an optical microscope. With respect to the wet form, the cellulose sponge was first soaked in deionized water, and then the pore morphology was observed by using an optical microscope.

Figure 2:
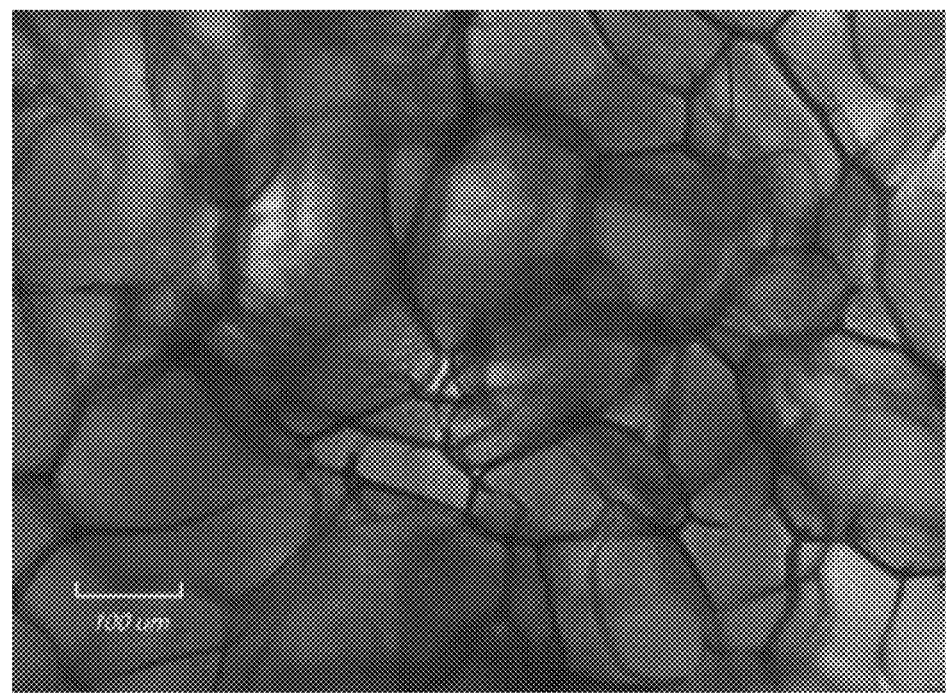
FIG. 2 is a magnified optical microscopy image of the cellulose sponge with additionally added alcohol of the present invention in dry form.
Figure 3:
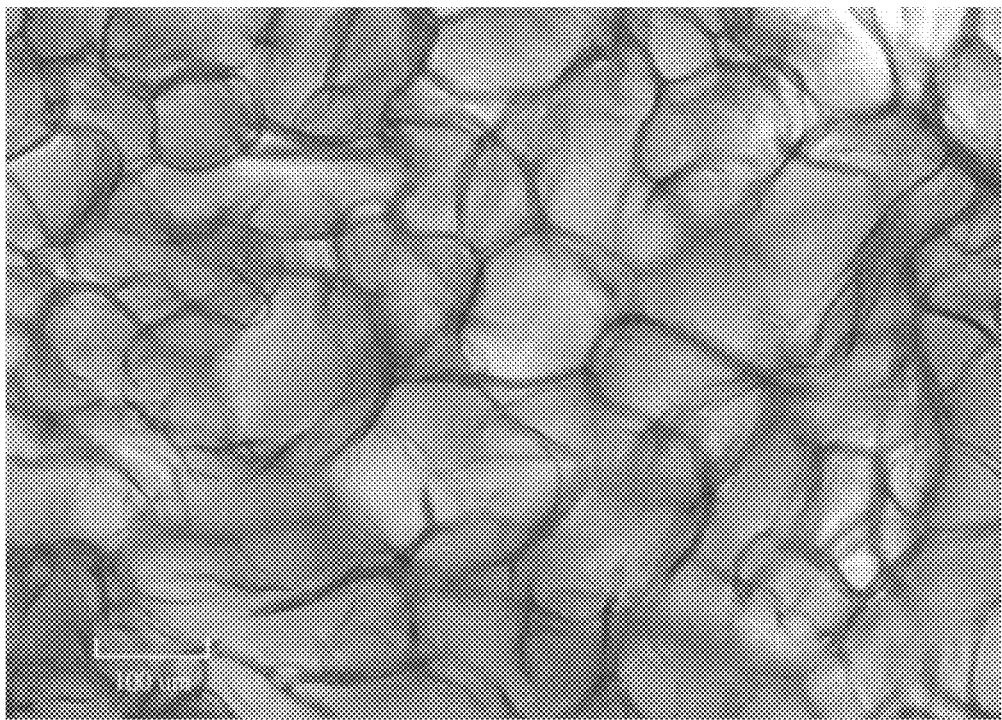
FIG. 3 is a magnified optical microscopy image of the cellulose sponge with additionally added alcohol of the present invention in wet form.

FIGS. 2 and 3 show optical microscopy images of the cellulose sponge with additionally added alcohol of the present invention in dry form as well as in wet form, indicating that there was no significant difference in the pore morphology between the dry form and the wet form. The structure of the pore wall was not affected after water was being added, which suggested that the pore morphology of the cellulose sponge with additionally added alcohol of the present invention was highly stable.

Figure 4:
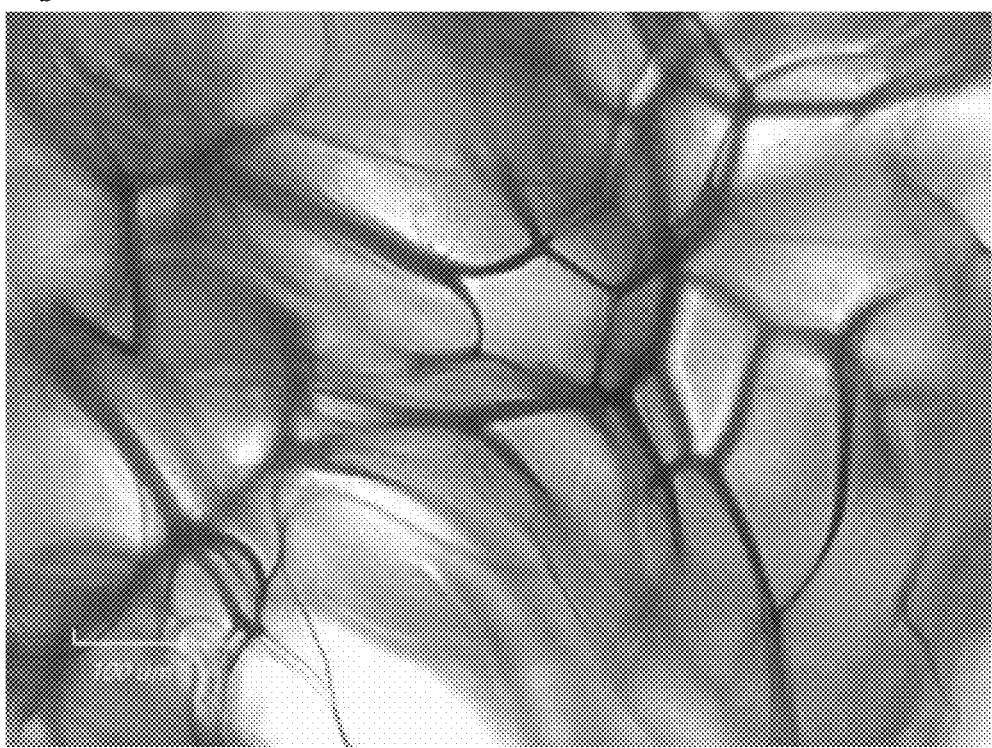
FIG. 4 is a magnified optical microscopy image of the cellulose sponge according to the present invention but without additionally added alcohol in dry form.
Figure 5:
FIG. 5 is a magnified optical microscopy image of the cellulose sponge according to the present invention but without additionally added alcohol in wet form.

FIGS. 4 and 5 show optical microscopy images of the cellulose sponge according to the present invention but without additionally added alcohol in dry form as well as in wet form, indicating that the structure of the pore wall of the cellulose sponge without additionally added alcohol in wet form was affected by water absorption. It was more difficult to observe the pore wall and the width was increased, which further reduced the pore volume. Accordingly, the stability of the pore morphology of the cellulose sponge according to the present invention but without additionally added alcohol was poor.

Applications of Cellulose Sponge

Cell culture conditions: HepG2 cells (human liver cancer cells), the medium was the high glucose Dulbecco's modified Eagle's medium (DMEM) supplemented with 10% fetal bovine serum, the cultivation conditions were 37° C. and 5% $CO_2$.

Step for inoculating cells: The cellulose sponge was placed in a 48-well plate, cell concentration of HepG2 was adjusted to $5 \times 10^6$ cells/ml, 60 μL was taken to be inoculated in the cellulose sponge, and after being placed in an incubator for 4 hours the cellulose sponge was removed from the incubator and 500 μL of culture medium was added. Subsequently the cellulose sponge was washed with phosphate buffer saline solution every three days and the fresh culture medium was added.

Figure 6:
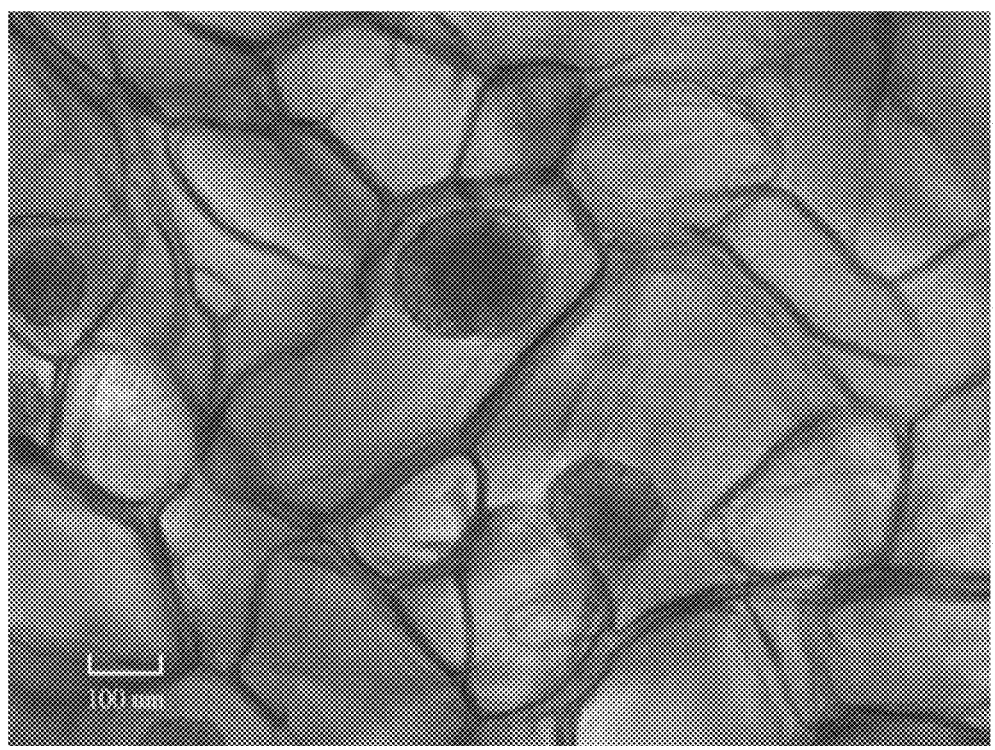
FIG. 6 is a magnified optical microscopy image of the cellulose sponge with additionally added alcohol of the present invention after cells being seeded.
Figure 7:
FIG. 7 is a magnified optical microscopy image of the cellulose sponge according to the present invention but without additionally added alcohol after cells being seeded.

FIGS. 6 and 7 are images observed 24 hours after HepG2 were seeded, FIG. 6 is the cellulose sponge with additionally added alcohol; FIG. 7 is the cellulose sponge without additionally added alcohol. They are magnified images observed the next day after HepG2 were inoculated using an optical microscope. It was found that, with respect to the cellulose sponge with additionally added alcohol of the present invention (FIG. 6), after the cells were inoculated the structure of the pore morphology was maintained and the cells were in a spheroid form, close to the actual pattern of the liver cells in human body. With respect to the cellulose sponge according to the present invention but without additionally added alcohol (FIG. 7), after cells were inoculated the structure of the pore morphology was not maintained, the pore size was significantly reduced, and the cells inclined to succumb to apoptosis. Therefore, it suggested that the pore morphology significantly affected the cell morphology.

Scanning Electron Microscopy Images of Cellulose Sponge Cross-Sectional Structure Method for preparing samples for scanning electron microscopy: After being wetted with deionized water, the cellulose sponge with additionally added alcohol was dehydrated with graded alcohols (50%, 70%, 90%, 100%), and finally treated with hexamethyldisilazane (HMDS), dried in a chemical fume hood.

Step for scanning electron microscopy: The prepared cellulose sponge was fixed on a carrier having an adhered conductive carbon gel, the surface was sputter coated with gold, and then the carrier was placed in a cavity under vacuum. Highly magnified scanning electron microscopy images were captured by using a computer.

Figure 8:
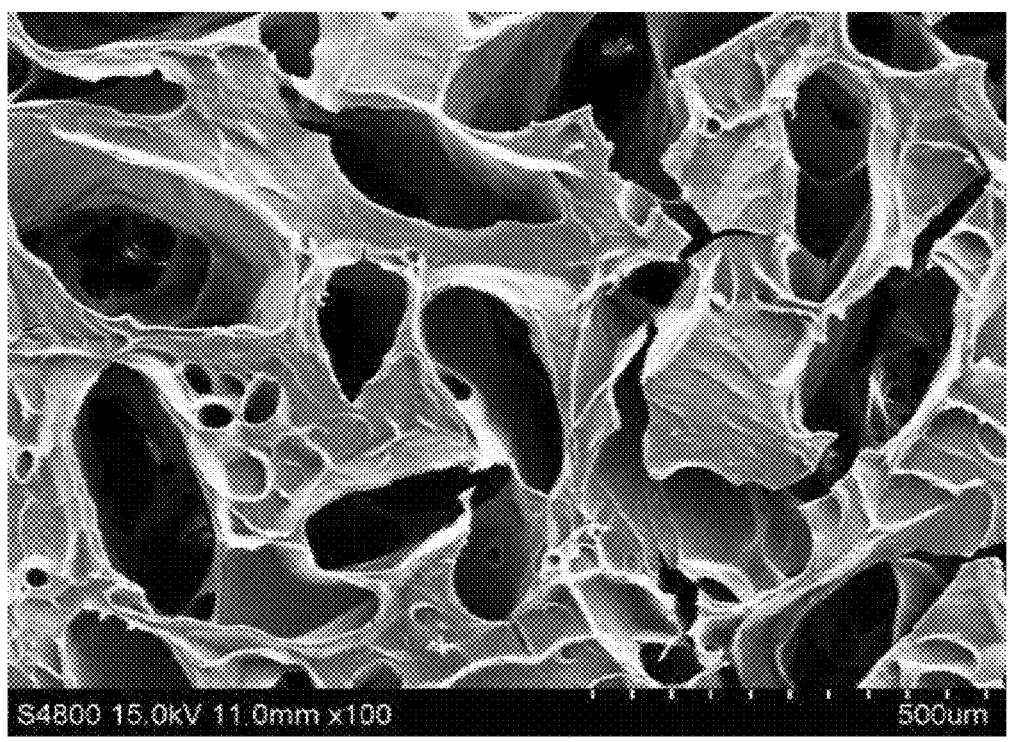
FIG. 8 is a scanning electron microscopy image of the cross-section of a cellulose sponge with additionally added alcohol of the present invention.

FIG. 8 is a scanning electron microscopy image of a cross-section of a cellulose sponge with additionally added alcohol, which indicated that the interior structure was an interconnected porous structure beneficial for cell growth therein. The porous structure not only provided an environment for cell growth and cell migration paths, allowed delivery of nutrients or signals to the cells in the interior of the cellulose sponge through the pores, but also provided channels to dispose metabolic wastes generated by the cells out of the cellulose sponge. Therefore, the porosity of the cellulose sponge provided an environment that was suitable for cell growth.

Confocal Microscopy of Cellulose Sponge Cross-Sectional Structure

Step for inoculating cells: The cellulose sponge with additionally added alcohol was placed in a 48-well plate, cell concentration of HepG2 was adjusted to $5\times10^6$ cells/ml, 60 µL was taken to be inoculated in the cellulose sponge, and after being placed in an incubator for 4 hours the cellulose sponge was removed from the incubator and 500 µL of culture medium was added. Washed with phosphate buffer saline solution after two days and then fresh culture medium was added.

Preparation of fluorescent dye: The fluorescent dye was formulated in compliance with the standard preparation procedure for fluorescent dyes, using the LIVE/DEAD® Viability/Cytotoxicity Assay Kit (Molecular Probes). 20 µL of 2 µM EthD-1 stock solution and 5 µL of 4 mM calcein AM stock solution were added to 10 ml of phosphate buffer saline solution, the fluorescent dye was produced after the mixture was homogenized.

Method for preparing samples for confocal microscopy: A cellulose sponge with additionally added alcohol was placed in a multi-well plate, 200 µL of fluorescent dye was added to each piece of cellulose sponge, reacted at room temperature for 30 minutes. The cellulose sponge was washed with phosphate buffer saline solution for several times and then the fluorescent dye was removed.

Step for using confocal microscope: The prepared cellulose sponge with additionally added alcohol was placed on a slide; a confocal microscope was used to observe red fluorescence and green fluorescence to determine whether the cells survived.

Figure 9:
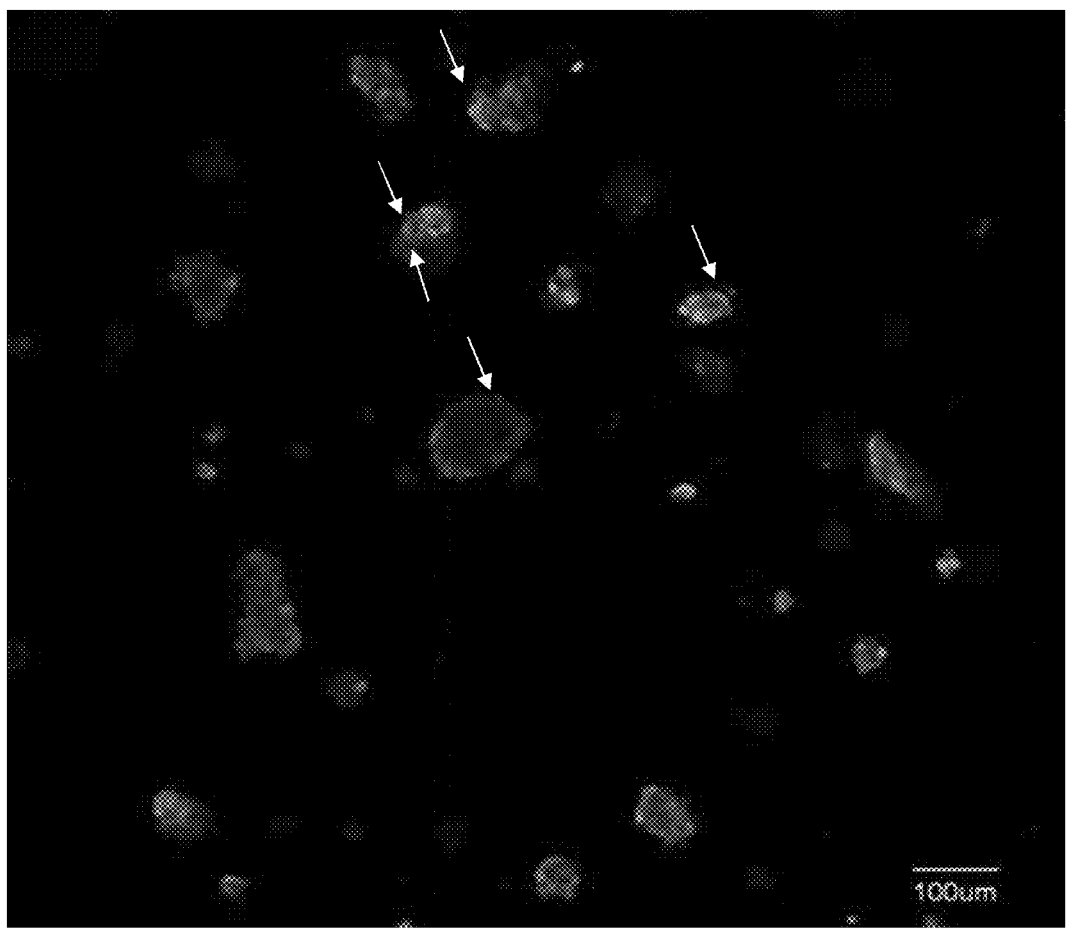
FIG. 9 is a confocal microscopy image of a cross-section of the cellulose sponge with additionally added alcohol of the present invention containing cells cultured therein.

FIG. 9 is a confocal microscopy image of a cross-section of a cellulose sponge with additionally added alcohol, which shows the result of the cellulose sponge after being cultivated for 3 days. The cell viability was determined by the fluorescent color. Green represented living cells, and red represented dead cells. As shown in the image, for those cells cultivated in the cellulose sponge with additionally added alcohol, most of them were in green (without arrows), very few of them were in red (at the arrows). Therefore, the survival rate was high after being cultivated for three days.

Cell Viability when Cultivated in Cellulose Sponge

Step for inoculating cells: The cellulose sponge with additionally added alcohol was placed in a 48-well plate, cell concentration of HepG2 was adjusted to $5\times10^6$ cells/ml, 60 µL was taken to be inoculated in the cellulose sponge, and after being placed in an incubator for 4 hours the cellulose sponge was removed from the incubator and 500 µL of culture medium was added. The cellulose sponge was washed with phosphate buffer saline solution every three days and then fresh culture medium was added.

Type of reagents used: Cell viability was quantified by using CELLTITER-GLO® 3D Cell Viability Assay (Promega). The reagent was completely formulated by mixing the CELLTITER-GLO® 3D reagent with a culture medium at a 1:1 ratio by volume.

200 µL of the mixed reagent was added to each piece of cellulose sponge. After 30 minutes of reaction, the luminescence data were read and recorded in relative luminescence units (RLUs). Higher RLUs indicated a better cell survival rate. The results are shown in Table 3.

TABLE 3

| | Cell viability | |
|---|---|---|
| | Cellulose sponge with additional added alcohol (RLU) | Cellulose sponge without additional added alcohol (RLU) |
| Day 1 | 1650054 | 11695 |
| Day 3 | 2496237 | 9726 |
| Day 5 | 3769120 | 8820 |

As shown in Table 3, the cell survival rate was detected by a luminescent reagent. Good cell growth was found in the cellulose sponge with additionally added alcohol and the cell count increased day by day, an indication of continued cell growth. Cell growth in the cellulose sponges according to the present invention but without additionally added alcohol was significantly poor on the first day, and the poor cell growth continued subsequently. Therefore, the cellulose sponge with additionally added alcohol of the present invention provided an environment in which good cells growth was enhanced.

What is claimed is:

1. A method for preparing a cellulose sponge, comprising:
   (A) dissolving hydroxypropyl cellulose in dimethylformamide to form a hydroxypropyl cellulose solution;
   (B) dissolving a compound comprising a self-crosslinkable substituent in dimethylformamide and adding it drop by drop into the hydroxypropyl cellulose solution;
   (C) adding alcohol for forming a mixed solution comprising dimethylformamide, hydroxypropyl cellulose, the compound comprising the self-crosslinkable substituent and alcohol to stabilize the pore morphology of the cellulose sponge;
   (D) drying at room temperature to form a hydroxypropyl cellulose having the self-crosslinkable substituent;
   (E) formulating the dried hydroxypropyl cellulose having the self-crosslinkable substituent into an aqueous solution; and
   (F) irradiating the aqueous solution of hydroxypropyl cellulose having the self-crosslinkable substituent with γ-ray for crosslinking thereby forming a cellulose sponge.

2. The method of claim 1, wherein the compound comprising the self-crosslinkable substituent comprises allyl isocyanate, methacrylic acid, acrylic acid, or glycidyl methacrylate.

3. The method of claim 1, wherein the volume of the alcohol is 1.5-50% of the total volume of the dimethylformamide.

4. The method of claim 1, wherein the volume of the alcohol is 7.5-40% of the total volume of the dimethylformamide.

5. The method of claim 1, wherein the volume of the alcohol is 10-35% of the total volume of the dimethylformamide.

6. A method of claim 1, wherein the alcohol is methanol, ethanol, propanol or butanol.

7. The method of claim 1, wherein the alcohol stabilizes the pore morphology of the cellulose sponge by controlling the size of pores.

8. The method of claim 7, wherein the size of the pores is 300 µm or less.

9. The method of claim 7, wherein the size of 73.6% of the pores is in the range of 101-200 µm.

* * * * *